(12) United States Patent
Kato et al.

(10) Patent No.: US 10,159,655 B2
(45) Date of Patent: Dec. 25, 2018

(54) AGENT FOR INHIBITING ODOR OF PYRAZINE DERIVATIVES

(71) Applicant: Kao Corporation, Tokyo (JP)

(72) Inventors: Aya Kato, Tochigi (JP); Naoko Saito, Utsunomiya (JP); Michiaki Inoue, Cincinnati, OH (US); Kayoko Nomizu, Chuo-ku (JP)

(73) Assignee: KAO Corporation, Tokyo (JP)

( * ) Notice: Subject to any disclaimer, the term of this patent is extended or adjusted under 35 U.S.C. 154(b) by 26 days.

(21) Appl. No.: 14/960,756

(22) Filed: Dec. 7, 2015

(65) Prior Publication Data

US 2016/0317470 A1 Nov. 3, 2016
US 2017/0258742 A9 Sep. 14, 2017

Related U.S. Application Data

(63) Continuation of application No. 13/693,178, filed on Dec. 4, 2012, now abandoned.

(60) Provisional application No. 61/596,963, filed on Feb. 9, 2012.

(51) Int. Cl.

| | | |
|---|---|---|
| A61K 31/121 | (2006.01) | |
| A61K 31/603 | (2006.01) | |
| A61K 31/045 | (2006.01) | |
| A61K 31/05 | (2006.01) | |
| A61K 31/11 | (2006.01) | |
| A61K 31/12 | (2006.01) | |
| A61K 31/09 | (2006.01) | |
| A61K 31/365 | (2006.01) | |
| A61K 31/122 | (2006.01) | |
| A61K 31/075 | (2006.01) | |
| C07D 241/12 | (2006.01) | |

(52) U.S. Cl.
CPC .......... *A61K 31/121* (2013.01); *A61K 31/045* (2013.01); *A61K 31/05* (2013.01); *A61K 31/075* (2013.01); *A61K 31/09* (2013.01); *A61K 31/11* (2013.01); *A61K 31/12* (2013.01); *A61K 31/122* (2013.01); *A61K 31/365* (2013.01); *A61K 31/603* (2013.01); *C07D 241/12* (2013.01)

(58) Field of Classification Search
CPC .................................................. C07D 241/12
See application file for complete search history.

(56) References Cited

U.S. PATENT DOCUMENTS

| | | | |
|---|---|---|---|
| 4,622,221 A | 11/1986 | Schleppnik | |
| 5,135,747 A | 8/1992 | Faryniarz et al. | |
| 5,272,134 A | 12/1993 | Berliner | |
| 6,086,903 A * | 7/2000 | Trinh .................. | A61K 8/02 424/401 |
| 6,432,891 B1 | 8/2002 | O'Connor | |
| 7,344,845 B2 | 3/2008 | Han et al. | |
| 7,425,445 B2 | 9/2008 | Matsunami et al. | |
| 7,481,891 B2 | 1/2009 | Higashi et al. | |
| 7,585,833 B2 | 9/2009 | Fadel et al. | |
| 7,875,258 B2 | 1/2011 | Babich et al. | |
| 8,506,943 B2 | 8/2013 | Payne et al. | |
| 8,741,275 B2 | 6/2014 | Dente et al. | |
| 9,012,153 B2 | 4/2015 | Kumihashi et al. | |
| 9,233,082 B2 | 1/2016 | Kato et al. | |
| 2003/0008787 A1* | 1/2003 | McGee .................. | A61K 8/37 510/101 |
| 2004/0223943 A1 | 11/2004 | Woo et al. | |
| 2008/0032913 A1 | 2/2008 | Finke et al. | |
| 2009/0010958 A1 | 1/2009 | Pinney | |
| 2010/0034766 A1 | 2/2010 | McGee et al. | |
| 2013/0210775 A1 | 8/2013 | Kato et al. | |

FOREIGN PATENT DOCUMENTS

| | | |
|---|---|---|
| EP | 0760243 A1 | 3/1997 |
| EP | 2110118 A1 | 10/2009 |
| EP | 1345883 B1 | 2/2010 |
| EP | 1909915 B1 | 3/2010 |
| GB | 2346900 A | 8/2000 |
| GB | 2359750 A | 9/2001 |
| JP | H11-241089 A | 9/1999 |
| JP | 2002-275495 A | 9/2002 |
| JP | 2003-24423 A | 1/2003 |
| JP | 2003-137758 A | 5/2003 |
| JP | 2003-339837 A | 12/2003 |
| JP | 2005-325055 A | 11/2005 |
| JP | 2006-124884 A | 5/2006 |
| JP | 2006-325902 A | 12/2006 |
| JP | 2012-050411 A | 3/2012 |
| JP | 2012-050781 A | 3/2012 |
| WO | WO 95/15186 A1 | 6/1995 |
| WO | WO 01/43784 A2 | 6/2001 |
| WO | WO 02/066083 A1 | 8/2002 |
| WO | WO 2005/046632 A2 | 5/2005 |

(Continued)

OTHER PUBLICATIONS

Bazemore, R. "Identification of Components Responsible for the Odor of Cigar Smoker's Breath" J. Agric. Food Chem. 2006, 54, 497-501.*
Alpert, H.R. et al. "A study of pyrazines in cigarettes and how additives might be used to enhance tobacco addiction" Tob Control 2015, 0, 1-7.*
Wicket, R. "How do sunless tanners work?" (https://www.scientificamerican.com/article/how-do-sunless-tanners-wo/) Apr. 12, 2004, p. 1. (Year: 2004).*
Adams, A. et al. J. Agric. Food Chem. 2008, 56, 2147-2153 (Year: 2008).*
Bazemore R., et al., "Identification of Components Responsible for the Odor of Cigar Smoker's Breath", J Agric Food Chem., Jan. 25, 2006, 54(2):497-501, 5 pgs.

(Continued)

*Primary Examiner* — Andrew S Rosenthal
(74) *Attorney, Agent, or Firm* — Frost Brown Todd, LLC (57) ABSTRACT

Provided is an agent for reducing odors of pyrazine derivatives based on an olfactory receptor antagonism. The agent for reducing odors of pyrazine derivatives includes at least one antagonist of olfactory receptor OR5K1 as an active ingredient.

7 Claims, 3 Drawing Sheets
Specification includes a Sequence Listing.

(56) References Cited

FOREIGN PATENT DOCUMENTS

| WO | WO 2008/026140 A2 | 3/2008 |
|---|---|---|
| WO | WO 2012/029922 A1 | 3/2012 |

OTHER PUBLICATIONS

BLAST, Basic Local Alignment Search Tool, "Appendix A: Alignment of instant SEQ IDS No. 4 with Han's SEQ ID No. 44," NCBI Blast: Protein Sequence (924 letters), May 18, 2015, 5 pgs.

Burdock, G.A., Ph.D., "2-Acetyl-3,5-Dimethylfuran", *Fenaroli's Handbook of Flavor Ingredients*, Sixth Ed., 2010, CRC Press, Taylor & Francis Group, Boca Raton, FL, USA, pp. 23-29 & 2009-2010, 11 pgs.

Cerny, C., et al., "Quantification of character-impact odour compounds of roasted beef", Z Lebensm Unters Forsch, May 1993, 196(5):417-422, 6 pgs.

Czerny, M., et al., "Sensory Study on the Character Impact Odorants of Roasted Arabica Coffee", J. Agric. Food Chem., 1999, 47(2):695-699, 5 pgs.

DeMaria, S., et al., "The cell biology of smell", JCB, 2010, 191(3):443-452, 10 pgs.

Department of Commerce, Patent and Trademark Office, "Supplementary Examination Guidelines for Determining Compliance with 35 U.S.C. 112 and for Treatment of Related Issues in Patent Applications," Federal Register, Feb. 9, 2011, 76(27):7162-7175, 14 pgs.

Hindenland, D.M., et al., "Reducing Odiferous Volatiles with Zeolites", Cosmetics & Toiletries, vol. 123, No. 7, Jul. 1, 2008. pp. 67-74, XP009167115.

Imahori, K, et al., "Skatole," Bichemistry dictionary, Mar. 1, 2000, The Fourth Impression of the $3^{rd}$ Ed., pp. 726-727.

Kawasaki, K., "Odor masking compositions containing fragrant substances for hair cosmetics" Database Caplus [Online] Chemical Abstracts Service, 2003. XP002719480.

Koehler, P.E., et al., "Odor Threshold Levels of Pyrazine Compounds and Assessment of Their Role in the Flavor of Roasted Foods", J. Food Sci., 1971, 36:816-818, 3 pgs.

Malnic, B. et al., "The human olfactory receptor gene family", PNAS, Feb. 24, 2004, vol. 101, No. 8, pp. 2584-2589.

Malnic, B., "Searching for the Ligands of Odorant Receptors", Mol Neurobiol (2007) 35:175-181.

Meierehenrich, U.J., et al., "The Molecular Basis of Olfactory Chemoreception", Angew Chem Int Ed. 2004, 43:6410-6412, 3 pgs.

Oka, Y., et al., "Olfactory receptor antagonism between odorants," The EMBO Journal, 2004, vol. 23, No. 1, pp. 120-126.

Oka, Y., et al., "The identification of the sense of smell receptor antagonist and physiologic signifcance," A Collection of Japan Society for Bioscience, Mar. 5, 2003, col. $2003^{rd}$, pp. 152.

OR5K1, olfactory receptor, family 5, subfamily K, member 1 [*Homo sapiens* (human)], Gene ID: 26339, updated on May 21, 2015, accessed Sep. 19, 2015 from http://www.ncbi.nlm.nih.gov/gene/26339, 6 pgs.

Ranau, R. et al., "Identification and evaluation of volatile odor-active pollutants from different odor emission sources in the food industry", European Food Research and Technology, Feb. 2005, 220(2):226-231, 6 pgs.

Saito, H., et al., "Odor coding by a Mammalian receptor repertoire," Sci. Signal., 2009, vol. 2, No. 60, ra9, pp. 1-28.

Sanz, G., et al., "Comparison of odorant specificity of two human olfactory receptors form different phylogenetic classes and evidence for antagonism," Chem. Senses, 2005, vol. 30, No. 1, pp. 69-80.

Shimazaki, K., et al., "Akylpyrazine-odor-blocking agents containing pyrazines", Database Caplus [Online] Chemical Abstracts Service, Jan. 28, 2003, XP002719444.

Shimazaki, K., et al., "Evaluation of the odor activity of pyrazine derivatives using structural and electronic parameters derived from conformational study by molecular mechanics (MM3) and ab initio calculations," Journal of Molecular Structure, 2005, 749:169-176, 8 pgs.

Tachihara, T., et al., "Studies on the Volatile Compunds of Roasted Spotted Shrimp", Chemistry & Biodiversity, 2004, 1:2024-2033, 10 pgs.

Touhara, K., "Function of the sense of smell receptor—Expression and function of the olfactory receptor gene superfamily." Igaku No Ayumi, Ushiyaku Pub. Inc., Jan. 1, 2005, vol. 212, No. 1, pp. 77-81.

Wagner, R.K., et al., "Key Odorants of French Fries", JAOCS, 1998, 785:1385-1392, 8 pgs.

Waller, G., and Feather, M. Eds., "The Maillard Reaction in Foods and Nutrition", ACS Symposium Series vol. 215, Apr. 29, 1983, Chapter 12, pp. 185-286.

Zhuang, H., et al., "Synergism of Accessory Factors in Functional Expression of Mammalian Odorant Receptors", Journal of Biological Chemistry, vol. 282, No. 20, May 1, 2007, pp. 15284-15293.

International Search Report and Written Opinion dated Feb. 13, 2014 for Application No. PCT/IB2012/003131.

International Search Report and Written Opinion dated Mar. 6, 2013 for Application No. PCT/US2012/067889.

International Search Report dated Sep. 7, 2012 for Application No. PCT/JP2012/064862.

U.S. Appl. No. 61/596,963, filed Feb. 9, 2012.

U.S. Appl. No. 61/636,093, filed Apr. 20, 2012.

\* cited by examiner

AGENT FOR INHIBITING ODOR OF PYRAZINE DERIVATIVES

CROSS-REFERENCE TO RELATED APPLICATIONS

This application claims priority from U.S. Provisional Patent Application No. 61/596,963, filed on Feb. 9, 2012, which is incorporated herein by reference in its entirety. This application is also a continuation of U.S. patent application Ser. No. 13/693,178, filed Dec. 4, 2012, which is incorporated herein by reference in its entirety.

FIELD OF THE INVENTION

The present invention relates to an agent for inhibiting an odor of a pyrazine derivative.

BACKGROUND OF THE INVENTION

There are a large number of malodorous molecules having different polarities and molecular weights in our living environment. Hitherto, a variety of methods have been developed for reducing various malodorous molecules. In general, the methods for reducing malodors are roughly classified into biological methods, chemical methods, physical methods, and sensory methods. Among malodorous molecules, short-chain fatty acids and amines having high polarities can be reduced by chemical methods, i.e., neutralization. Sulfur compounds such as thiol can be reduced by physical methods, i.e., absorptive treatment. However, there are still many malodorous molecules which cannot be reduced by known malodor reducing methods.

In addition, the known malodor reducing methods by the chemical neutralization or the absorptive treatment take long time for reducing the amounts of malodorous substances and thereby lack immediate effect. A method of reducing malodor by using an aromatic and thereby providing strong perception of another odor is also known. However, the odor of the aromatic may cause discomfort in this method. Moreover, these known methods may get rid of odors other than the target malodors. Thus, there is a demand for a malodor reducing method which can overcome these problems.

In mammals including humans, the mechanism for odorant recognition includes binding odorant molecules to olfactory receptors present on olfactory sensory neurons included in the olfactory epithelium, which is present in an upper portion of the nasal cavity, and transmitting the response of the receptors to the central nervous system. It has been reported that, 387 different olfactory receptors are present in human, and the genes encoding these olfactory receptors account for about 3% of the human genome. In general, a plurality of olfactory receptors responds to a plurality of odorant molecules. Specifically, one single olfactory receptor responds to a plurality of structurally similar odorant molecules at different affinities, while one single odorant molecule is detected by a plurality of olfactory receptors. It is also reported that a certain odorant molecule which can activate one olfactory receptor serves as an antagonist which inhibits activation of another olfactory receptor. Such combined response of these olfactory receptors leads to recognition of each odor.

Thus, when a first odorant molecule is co-present with a second odorant molecule, in some cases, the response of an olfactory receptor to the first odorant molecule is inhibited by the second odorant molecule. Through the inhibition, the odor of the first odorant molecule recognized by olfactory receptors may vary considerably. This mechanism is called "olfactory receptor antagonism." Odor modulation by olfactory receptor antagonism can inhibits recognition specific to a malodor, and therefore differs in mechanism from a malodor reducing method by adding a perfume, an aromatic, or a like substance to the target odorant. In addition, the odor of an aromatic causing an unpleasant sensation to users can be prevented. Therefore, odor modulation based on olfactory receptor antagonism is a preferred means for reducing malodor.

In order to mask a malodor with an odor of, for example, a perfume or an aromatic, it is necessary to identify an odor substance exhibiting an effective malodor reducing function on the target malodorous substance. Hitherto, odors have been evaluated through a sensory test by specialists. However, the sensory test has problems. The problems include for example, odor-evaluators must be trained, and the throughput of the test is low. Thus, identification of an odor substance exhibiting a malodor reducing function is not easy.

A skin tanning agent (also called a self-tanning agent or a sunless tanning agent) is a skin cosmetic for staining the skin. As a component for providing skin with a brown color, dihydroxyacetone (DHA) is mainly used alone or together with, for example, erythrulose. These components react with the upper layer of the skin to change the color of skin to brown. This staining probably progresses by a browning reaction, but the details of the reaction mechanism have been hardly clarified. The browning reaction is also called a Maillard reaction in the food chemistry field and is a term referring to a reaction for generating a brown polymer called melanoidin by polymerizing a nitrogen-containing compound, such as an amino acid or a protein, and a reducing sugar. The Maillard reaction is caused by, for example, heating of a food and is involved in coloring of the food and generation of a flavor component.

Pyrazines are known to be generated by the Maillard reaction and as a component of a roasted aroma of a food. Patent Document 1 describes an odor-blocking agent including a functional pyrazine compound as an active ingredient for blocking the odor of an alkylpyrazine compound. Pyrazines are usually used as flavoring agents for flavoring foods, and the odors of pyrazines are rather utilized. In the food field, odors obtained by the Maillard reaction are reported in Non-Patent Document 1. In Non-Patent Document 1, the pyrazine compound is described as a preferred odor which characterizes a food. For example, 2,6-dimethylpyrazine is described as having a "sweet, fried, resembling fried potatoes, nutty, roasted" odor.

PRIOR ART

Patent Documents

[Patent Document 1] JP-A-2003-024423

Non-Patent Documents

[Non-Patent Document 1] S. Fors, Sensory Properties of Volatile Maillard Reaction Products and Related Compounds, "The Maillard Reaction in Foods and Nutrition" (ACS Symposium Series, Vol. 215), Chapter 12, pp. 185-286 Publication Date (Print): Apr. 29, 1983

SUMMARY OF THE INVENTION

The present invention provides use of at least one compound selected from the group consisting of compounds described in Table 1 below, for reducing an odor of a pyrazine derivative.

The present invention also provides a method of reducing an odor of a pyrazine derivative, wherein the method includes coexisting an odor of a pyrazine derivative with at least one compound selected from the group consisting of compounds described in Table 1 below.

The present invention further provides an agent for reducing an odor of a pyrazine derivative, including at least one antagonist against olfactory receptor OR5K1 as an active ingredient, wherein the antagonist is selected from the group consisting of compounds described in Table 1 below.

TABLE 1

2-ethyl-4-(2,2,3-trimethyl-3-cyclopenten-1-yl)-2-buten-1-ol
5-methyl-2-(1-methylethyl)-phenol
3,7-dimethyl-2,6-octadienal
phenylethyl salicylate
1-(5,6,7,8-tetrahydro-3,5,5,6,8,8-hexamethyl-2-naphthalenyl)-ethanone
isolongifolanone
4-(2,6,6-trimethyl-2-cyclohexen-1-yl)-3-buten-2-one (α-ionone)
4-(2,6,6-trimethyl-1-cyclohexen-1-yl)-3-buten-2-one (β-ionone)
vetiverol
7-acetyl-1,2,3,4,5,6,7,8-octahydro-1,1,6,7-tetramethyl-naphthalene
α-amylcinnamic aldehyde
α-methyl-4-(1-methylethyl)-benzenepropanal
4-methyl-3-decen-5-ol
1-(2-tert-butylcyclohexyloxy)-2-butanol
2-methoxy-1-(phenylmethoxy)-4-(1-propenyl)-benzene
α-methyl-β-(p-tert-butylphenyl)-propionaldehyde
1(−)-menthol
ω-6-hexadecenelactone
2-(2-(4-methyl)-3-cyclohexen-1-yl)-propylcyclopentanone
formaldehyde cyclododecyl ethyl acetal
1-(2,3,4,7,8,8a-hexahydro-3,6,8,8-tetramethyl-1H-3a,7-methanoazulen-5-yl)-ethanone
β-methyl naphthyl ketone
cedryl acetate
(5E)-3-methylcyclopenta-5-decen-1-one
cinnamaldehyde
4-(1-ethoxyvinyl)-3,3,5,5-tetramethylcyclohexanone
α-hexylcinnamic aldehyde
2-phenylpropionaldehyde
3,7-dimethyl-6-octenal
dodecahydro-3a,6,6,9a-tetramethylnaphtho[2,1-b]furan
4,7,7-trimethyl-spirobicyclo[2.2.1]heptane-2,1-cyclopentan-3-one
α-isomethyl ionone
3,7-dimethyl-1-octanol
cedryl methyl ether
muscone
2-methyl-4-(2,2,3-trimethyl-3-cyclopenten-1-yl)-2-buten-1-ol
2-cyclohexylpropanal
γ-undecalactone
Cyclopentadecanolide
1-(2,6,6-trimethyl-1,3-cyclohexadien-1-yl)-2-buten-1-one
2,4-dimethyl-3-cyclohexene-1-carboxyaldehyde
2,4,6-trimethyl-3-cyclohexene-1-carboxyaldehyde
3,5,6-trimethyl-3-cyclohexene-1-carboxyaldehyde
6,10-dimethyl-3-oxa-9-undecenal
dimethyl benzyl carbinyl acetate
ethyl-(3aα,4α,7α,3aα)-octahydro-4,7-methano-3aH-indene-3a-carboxylate
2-pentyl-3-methyl-2-cyclopenten-1-one
phenylhexanol TABLE 1-continued 1-(5,5-dimethyl-1-cyclohexen-1-yl)-4-penten-1-one
6-tert-butyl-1,1-dimethylinden-4-yl methyl ketone
cis-4-isopropylcyclohexylmethanol
1-allyl-3-methoxy-4-hydroxybenzene
(E)-3,7-dimethyl-2,6-octadien-1-ol
4-tert-butyl-2,6-dimethyl-3,5-dinitroacetophenone
1,4-dioxacycloheptadecane-5,17-dione
hexyl salicylate
α-methyl-3,4-methylenedioxyhydrocinnamic aldehyde

DETAILED DESCRIPTION OF THE INVENTION

A problem that the use of a commercially available skin tanning agent (self-tanning agent or sunless tanning agent) involves a characteristic unpleasant odor expressed as, for example, an earthy or burnt sugar odor has been reported (D. M. Hindenlang and M. E. McDonnell, Cosmetics & Toiletries magazine, 2008, Vol. 123, No. 7, pp. 67-74), and there has been a demand for improvement thereof. The cause of the unpleasant odor was investigated to reveal that dimethylpyrazine, which is generated when dihydroxyacetone (DHA) or erythrulose in a skin tanning agent reacts with the skin to change the color of skin to brown, is one of causative substances. Furthermore, it revealed that, in addition to dimethylpyrazine, other pyrazine derivatives yield similar odors, and there is a demand for reducing the odors of these pyrazine derivatives.

In order to attain the olfactory receptor antagonism, an olfactory receptor which responds to a target malodorous substance must be determined, and a substance which effectively exhibits an antagonistic effect on an olfactory receptor of malodorous substance must be searched and identified. Accordingly, the present inventors searched for an olfactory receptor which responds to a pyrazine derivative and succeeded in identification of the receptor. Furthermore, the present inventors found that the substance which inhibits response of the olfactory receptor can reduce the odor of the pyrazine derivative through masking by the olfactory receptor antagonism.

According to the present invention, odors of pyrazine derivatives, for example, the odor which is generated in the use of a known self-tanning agent (also called a sunless tanning agent) can be specifically reduced without causing problems occurring in known malodor reducing methods using a deodorant or an aromatic, such as lack of immediate effect and discomfort due to the odor of the aromatic.

As used herein, the term "masking" in the odor-related field generally refers to means for inhibiting or weakening recognition of a target odor. The term "masking" may encompass chemical means, physical means, biological means, and sensory means. Examples of the masking means include any means for removing a odorant molecule responsible for a target odor from the environment (e.g., adsorption and chemical decomposition of the odorant); means for preventing release of a target odor to the environment (e.g., sealing); and a method in which recognition of a target odor is reduced by adding another odorant such as a flavoring agent or an aromatic.

As used herein, the term "masking through olfactory receptor antagonism" refers to one embodiment of the aforementioned broadly defined "masking" and is means for inhibiting the response of an olfactory receptor to a target odorant molecule by an additional odorant molecule, to thereby modulate the odor of the target odorant molecule recognized by a subject. Although masking through olfactory receptor antagonism employs an additional odorant molecule, the masking differs from means for canceling out a target odor by use of a strong odorant such as an aromatic. In one embodiment of masking through olfactory receptor antagonism, a substance which can inhibit the response of an olfactory receptor such as an antagonist is used. When a response-inhibiting substance which can specifically inhibit the response of a receptor related to recognition of a certain odor is employed, the response of the receptor is suppressed, whereby the odor recognized by a subject can be modulated.

The present inventors identified olfactory receptor OR5K1 from many olfactory receptors as a sole receptor which responds to pyrazine derivatives. The response of OR5K1 to pyrazine derivatives has not been found until now, and OR5K1 is a novel receptor for the pyrazine derivatives.

Figure 1:
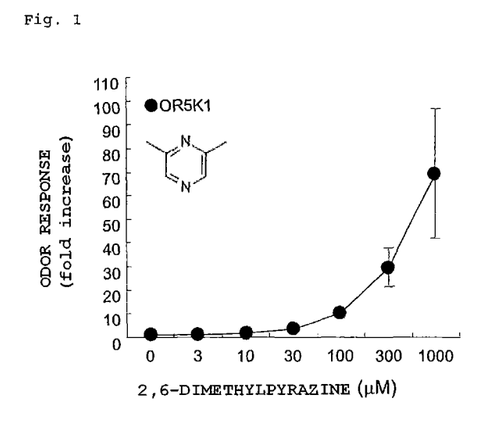
FIG. 1 shows responses of olfactory receptor OR5K1 to various concentrations of 2,6-dimethylpyrazine, wherein n=5 and error bar=±SE.
Figure 2:
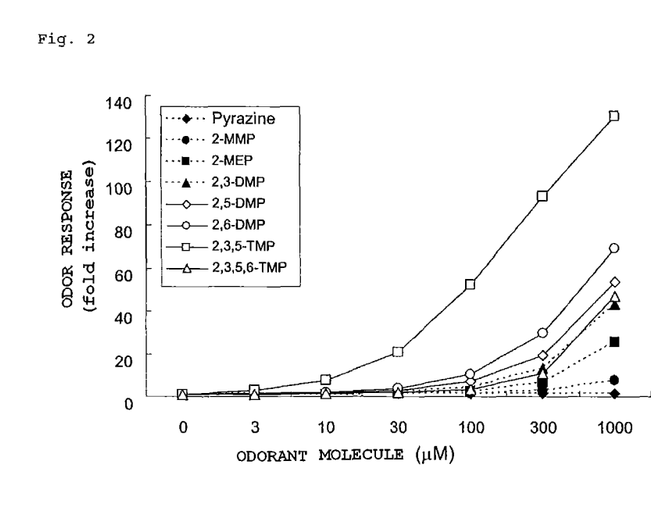
FIG. 2 shows responses of olfactory receptor OR5K1 to various concentrations of pyrazine compounds, wherein n=3 to 5 and error bar=±SE.

As shown in FIGS. 1 and 2, OR5K1 responds to pyrazine derivatives represented by Formula (I) in dose-dependent manner. Consequently, a substance which inhibits the response of OR5K1 causes a change in perception of the odor of pyrazine derivatives in the central nervous system by masking based on the olfactory receptor antagonism and, as a result, can reduce the odor in an odor-specific manner.

An aspect of the present invention provides an agent for reducing an odor of a pyrazine derivative, wherein the agent includes an antagonist of olfactory receptor OR5K1 for pyrazine derivatives as an active ingredient. Olfactory receptor OR5K1 is expressed in human olfactory cells and has been registered in GenBank under the accession number GI: 115270955. OR5K1 is a protein encoded by a gene having a nucleotide sequence represented by SEQ ID NO: 1 and having the amino acid sequence represented by SEQ ID NO: 2.

"Pyrazine derivatives" in the present invention are compounds represented by the following Formula (I):

In Formula (I), $R_1$ represents methyl, ethyl, or acetyl; and $R_2$, $R_3$, and $R_4$ each independently represent hydrogen or methyl. At least one of $R_1$ to $R_4$ is preferably an alkyl group. Examples of the pyrazine represented by Formula (I) of the present invention include 2,6-dimethylpyrazine, 2,5-dimethylpyrazine, 2,3-dimethylpyrazine, 2,3,5-trimethylpyrazine, 2,3,5,6-tetramethylpyrazine, 2-monomethylpyrazine, 2-monoethylpyrazine, 2-ethyl-6-methylpyrazine, 3-methyl-2-acetylpyrazine, and 3,5-dimethyl-2-acetylpyrazine.

In the present invention, the "odor of a pyrazine derivative" can be an odor due to a pyrazine derivative represented by Formula (I). The "odor of a pyrazine derivative" in the present invention can be an odor generated by a Maillard reaction and is typically described as a roasted odor and the like. For example, Non-Patent Document 1 discloses that 2,6-dimethylpyrazine has "sweet, fried, resembling fried potatoes, nutty, roasted" odors. In addition, the "odor of a pyrazine derivative" in the present invention can be expressed as an odor generated in the use of a known self-tanning agent, more specifically, an earthy odor or an odor generated when dihydroxyacetone (DHA) or erythrulose reacts with the skin to change the color of skin to brown.

The antagonist can block the response of olfactory receptor OR5K1 to a pyrazine derivative represented by Formula (I) by 40% or more, preferably 50% or more, and more preferably 75% or more, compared to the response in the absence of the antagonist. In other words, the response of olfactory receptor OR5K1 to the pyrazine derivative in the presence of the antagonist is reduced to 60% or less, preferably 50% or less, or more preferably 25% or less of the response of the receptor in the absence of the antagonist.

Examples of the antagonist as an active ingredient of the agent for reducing an odor of a pyrazine derivative according to the present invention include the following substances:

2-ethyl-4-(2,2,3-trimethyl-3-cyclopenten-1-yl)-2-buten-1-ol (bacdanol);
5-methyl-2-(1-methylethyl)-phenol (thymol);
3,7-dimethyl-2,6-octadienal (citral);
phenylethyl salicylate;
1-(5,6,7,8-tetrahydro-3,5,5,6,8,8-hexamethyl-2-naphthalenyl)-ethanone (Tonalid (registered trademark), tentarome);
isolongifolanone;
4-(2,6,6-trimethyl-2-cyclohexen-1-yl)-3-buten-2-one (α-ionone);
4-(2,6,6-trimethyl-1-cyclohexen-1-yl)-3-buten-2-one (β-ionone);
vetiverol;
7-acetyl-1,2,3,4,5,6,7,8-octahydro-1,1,6,7-tetramethyl-naphthalene (Iso E Super);
α-amylcinnamic aldehyde;
α-methyl-4-(1-methylethyl)-benzenepropanal (cyclamen aldehyde);
4-methyl-3-decen-5-ol (undecavertol);
1-(2-tert-butylcyclohexyloxy)-2-butanol (Amber Core (registered trademark));
2-methoxy-1-(phenylmethoxy)-4-(1-propenyl)-benzene (benzyl isoeugenol);
α-methyl-β-(p-tert-butylphenyl)-propionaldehyde (lilial);
1(-)-menthol;
ω-6-hexadecenelactone (ambrettolide);
2-(2-(4-methyl)-3-cyclohexen-1-yl)-propylcyclopentanone (nectaryl);
formaldehyde cyclododecyl ethyl acetal (Boisambrene Forte (registered trademark));
1-(2,3,4,7,8,8a-hexahydro-3,6,8,8-tetramethyl-1H-3a,7-methanoazulen-5-yl)-ethanone (acetyl cedrene);
3-methyl naphthyl ketone;
cedryl acetate;
(5E)-3-methylcyclopenta-5-decen-1-one (6-muscenone);
cinnamaldehyde;
4-(1-ethoxyvinyl)-3,3,5,5-tetramethylcyclohexanone (kephalis);
α-hexylcinnamic aldehyde;
2-phenylpropionaldehyde (hydratropic aldehyde);
3,7-dimethyl-6-octenal (citronellal);

dodecahydro-3a,6,6,9a-tetramethylnaphtho[2,1-b]furan (Ambrotech (registered trademark));
4,7,7-trimethyl-spirobicyclo[2.2.1]heptane-2,1-cyclopentan-3-one (Sagetone (registered trademark) V);
α-isomethyl ionone (γ-methyl ionone);
3,7-dimethyl-1-octanol (tetrahydrogeraniol);
cedryl methyl ether;
muscone;
2-methyl-4-(2,2,3-trimethyl-3-cyclopenten-1-yl)-2-buten-1-ol (Sandalmysore Core (registered trademark));
2-cyclohexylpropanal (Pollenal (registered trademark) II);
γ-undecalactone;
cyclopentadecanolide (pentalide);
1-(2,6,6-trimethyl-1,3-cyclohexadien-1-yl)-2-buten-1-one (damascenone);
2,4-dimethyl-3-cyclohexene-1-carboxyaldehyde (triplal);
2,4,6-trimethyl-3-cyclohexene-1-carboxyaldehyde or 3,5,6-trimethyl-3-cyclohexene-1-carboxyaldehyde (isocyclocitral);
6,10-dimethyl-3-oxa-9-undecenal (citronellyloxyacetaldehyde);
dimethyl benzyl carbinyl acetate;
ethyl-(3aα,4α,7α,3aα)-octahydro-4,7-methano-3aH-indene-3a-carboxylate (Fruitate (registered trademark));
2-pentyl-3-methyl-2-cyclopenten-1-one (dihydrojasmon);
phenylhexanol;
1-(5,5-dimethyl-1-cyclohexen-1-yl)-4-penten-1-one (Dynascone (registered trademark));
6-tert-butyl-1,1-dimethylinden-4-yl methyl ketone (celestolide);
cis-4-isopropylcyclohexylmethanol (mayol);
1-allyl-3-methoxy-4-hydroxybenzene (eugenol);
(E)-3,7-dimethyl-2,6-octadien-1-ol (geraniol);
4-tert-butyl-2,6-dimethyl-3,5-dinitroacetophenone (musk ketone);
1,4-dioxacycloheptadecane-5,17-dione (ethylene brassylate);
hexyl salicylate; and
α-methyl-3,4-methylenedioxyhydrocinnamic aldehyde (helional).

Among the above-mentioned antagonists, preferred examples as the active ingredient of the agent for reducing an odor of a pyrazine derivative according to the present invention include 2-ethyl-4-(2,2,3-trimethyl-3-cyclopenten-1-yl)-2-buten-1-ol (bacdanol); 5-methyl-2-(1-methylethyl)-phenol (thymol); 3,7-dimethyl-2,6-octadienal (citral); phenylethyl salicylate; 1-(5,6,7,8-tetrahydro-3,5,5,6,8,8-hexamethyl-2-naphthalenyl)-ethanone (Tonalid (registered trademark), tentarome); isolongifolanone; 4-(2,6,6-trimethyl-2-cyclohexen-1-yl)-3-buten-2-one (α-ionone); 4-(2,6,6-trimethyl-1-cyclohexen-1-yl)-3-buten-2-one (β-ionone); vetiverol; 7-acetyl-1,2,3,4,5,6,7,8-octahydro-1,1,6,7-tetramethyl-naphthalene (Iso E Super); α-amylcinnamic aldehyde; α-methyl-4-(1-methylethyl)-benzenepropanal (cyclamen aldehyde); 4-methyl-3-decen-5-ol (undecavertol); and 1-(2-tert-butylcyclohexyloxy)-2-butanol (Amber Core (registered trademark)).

As the active ingredient of the agent for reducing an odor of a pyrazine derivative according to the present invention may be at least one selected from the above-mentioned antagonists. That is, the above-mentioned antagonists are contained in the agent for reducing an odor of a pyrazine derivative of the present invention alone or in a combination of two or more thereof. Preferably, the agent for reducing an odor of a pyrazine derivative of the present invention is essentially composed of any one of the above-mentioned antagonists or a combination of two or more of the above-mentioned antagonists.

As shown in Table 4, these substances are antagonists of olfactory receptor OR5K1 and inhibit the response of the olfactory receptor to pyrazine derivatives represented by Formula (I). The substances have been known as flavoring raw materials, but have not been known to have a function of blocking response of an olfactory receptor to pyrazine derivatives and thereby reducing the odors of the pyrazine derivatives.

The above-mentioned antagonists are commercially available (see "Gosei Koryo (Synthetic Flavoring Materials): Kagaku to Syohin Chishiki (Chemistry and Knowledge on Products)", enlarged and revised edition, by Genichi Indo, The Chemical Daily Co., Ltd., published in March, 2005). For example, they are available from Firmenich S. A., Givaudan S. A., International Flavors & Fragrances Inc., Takasago International Corporation, and Kao Corporation.

In another aspect of the present invention, the above-mentioned antagonists of olfactory receptor OR5K1 can be contained in compounds or compositions for reducing the odor of pyrazine derivatives as active ingredients for reducing the odors of the pyrazine derivatives. Alternatively, the antagonists can be used for producing agents for reducing odors of pyrazine derivatives or for producing compounds or compositions for reducing the odor of pyrazine derivatives.

The agent, the compound, or the composition for reducing the odor of a pyrazine derivatives described above may contain, in addition to the substance of the present invention, another component having a malodor reducing effect or an appropriate component used in a deodorant or a deodorizer. For example, a flavoring agent, a powder component, a liquid oil or fat, a solid oil or fat, a wax, a hydrocarbon, a plant extract, a Chinese medicine component, a higher alcohol, a lower alcohol, an ester, a long-chain fatty acid, a surfactant (e.g., nonionic surfactant, anionic surfactant, cationic surfactant, or ampholytic surfactant), a sterol, a polyol, a moisturizer, a water-soluble high-molecular-weight compound, a thickener, a film-forming agent, a sterilizer, a preservative, an anti-fungal agent, a ultraviolet absorber, a fixing agent, a cold-sensing agent, a warm-sensing agent, a stimulant, a sequestering agent, sugar, an amino acid, an organic amine, a synthetic resin emulsion, a pH adjuster, an antioxidant, an antioxidant auxiliary, an oil, a powder, a capsule, a chelating agent, an inorganic salt, an organic salt dye, a colorant, an antifoaming agent, a bulking agent, a modulator, an organic acid, a polymer, a polymer-dispersing agent, an enzyme, or an enzyme stabilizer may be appropriately contained according to the object.

The another component having a malodor reducing effect which can be contained in the agent, the compound, or the composition for reducing an odor of a pyrazine derivative may be any known deodorant having a chemically or physically malodor reducing effect. Examples of the component include malodor reducing active ingredients extracted from each part of plants, such as a leaf, a leafstalk, a seed, a stalk, a root, and a bark (e.g., green tea extract); organic acids such as lactic acid, gluconic acid, succinic acid, glutanic acid, adipic acid, malic acid, tartaric acid, maleic acid, fumaric acid, itaconic acid, citric acid, benzoic acid, and salicylic acid; various amino acids and salts thereof; glyoxal, oxidizing agents, flavonoids, catechins, and polyphenols; porous materials such as activated carbon and zeolite; inclusion agents such as cyclodextrins; photocatalysts; and various masking agents.

In another aspect of the present invention, the above-mentioned antagonists of olfactory receptor OR5K1 can be used as active ingredients for reducing odors of pyrazine derivatives in every compound or composition desired to reduce the odor of the pyrazine derivatives or under every environment desired to reduce the odor of the pyrazine derivatives. Alternatively, the antagonists can be used for producing compounds or compositions desired to reduce the odor of pyrazine derivatives as active ingredients for reducing the odors of the pyrazine derivatives. Examples of the compounds or the compositions desired to reduce the odor of the pyrazine derivatives include skin tanning agents (also called self-tanning agent or sunless tanning agent), for example, a skin tanning agent containing dihydroxyacetone (DHA) or erythrulose as a color former and another skin tanning agent utilizing a browning reaction. The pyrazine derivatives may be contained in foods as flavoring components and may cause off-flavors if their amounts are high. Accordingly, other examples of the compounds or the compositions desired to reduce the odor of the pyrazine derivatives include foods containing the pyrazine derivatives as flavoring components and compositions thereof, more specifically, foods, such as roasted peanuts and milk powders, of which taste is reduced by the presence of excess amounts of pyrazine derivatives and compositions thereof.

As further another aspect, the present invention provides a method of reducing an odor of a pyrazine derivative. The method includes a step of allowing an odor of a pyrazine derivative and an antagonist of olfactory receptor OR5K1 to coexist. In the method, an antagonist of olfactory receptor OR5K1 is applied, in the presence of the odor of pyrazine derivatives, to an individual desiring to inhibit perception of the odor, preferably, an individual desiring to inhibit perception of the odor of pyrazine derivatives through masking by the olfactory receptor antagonism, and thereby the odor of pyrazine derivatives and the antagonist are allowed to coexist. Consequently, the antagonist binds to OR5K1 to inhibit the response of OR5K1, and thereby masking by the olfactory receptor antagonism occurs to reduce the odor of pyrazine derivatives.

Preferred antagonists in the method of the present invention are similar to the above-described agents for reducing the odor of the pyrazine derivatives.

In the method of the present invention, the individual is not particularly limited but may be any mammal and is preferably human. Examples of the individual desiring to inhibit perception of an odor of a pyrazine derivative in the method of the present invention include human using a skin tanning agent (or self-tanning agent or sunless tanning agent), more specifically, a skin tanning agent containing dihydroxyacetone (DHA) or erythrulose as a color former or another skin tanning agent utilizing a browning reaction and human desiring to reduce an odor of a pyrazine derivative from a food, for example, human ingesting a food, such as a roasted peanut or a milk powder, of which taste is reduced by the presence of an excess amount of the pyrazine derivative.

In an embodiment of the above-described aspect, the antagonist of olfactory receptor OR5K1 is blended with a compound or a composition containing a pyrazine derivative. By doing so, the response of an olfactory receptor to the pyrazine derivative contained in the compound or the composition is reduced to inhibit the perception of the pyrazine derivative odor by the individual, resulting in reduction of the odor.

In another embodiment, the antagonist of olfactory receptor OR5K1 is blended with a compound or a composition which may generate a pyrazine derivative. By doing so, the response of the olfactory receptor to the pyrazine derivative generated by the compound or the composition is reduced to inhibit the perception of the pyrazine derivative odor by the individual, resulting in reduction of the odor. Examples of the compound or the composition which may generate a pyrazine derivative include skin tanning agents, for example, a skin tanning agent containing dihydroxyacetone (DHA) or erythrulose as a color former and another skin tanning agent utilizing a browning reaction.

The following compositions, production methods, usages or methods are further disclosed herein as another embodiment of the present invention, that are, however, not intended to limit the scope of the present invention.

<1> Use of at least one compound selected from the group consisting of compounds described in Table 1 above, as an antagonist of olfactory receptor OR5K1.

<2> Use of at least one compound selected from the group consisting of compounds described in Table 1 above, for reducing an odor of a pyrazine derivative.

<3> Use of at least one compound selected from the group consisting of compounds described in Table 1 above, for producing an agent for reducing an odor of a pyrazine derivative.

<4> Use of at least one compound selected from the group consisting of compounds described in Table 1 above, for producing a skin tanning agent.

<5> A method of reducing an odor of a pyrazine derivative, wherein the method includes coexisting an odor of a pyrazine derivative with at least one compound selected from the group consisting of compounds described in Table 1 above.

<6> The method according to <5>, which includes applying the at least one compound to an individual in need of reduction of odor of the pyrazine derivative in the presence of the odor of the pyrazine derivative.

<7> The method according to <6>, wherein the at least one compound inhibits responses of an olfactory receptor OR5K1.

<8> A method of antagonizing responses of an olfactory receptor OR5K1, wherein the method includes applying, to an olfactory receptor OR5K1, at least one compound selected from the group consisting of compounds described in Table 1 above.

<9> In any of <2> to <8>, the pyrazine derivative may be a compound represented by the following formula (I):

wherein $R_1$ represents methyl, ethyl or acetyl; and $R_2$, $R_3$ and $R_4$ each independently represent hydrogen or methyl.

<10> In <9>, at least one of $R_1$ to $R_4$ may represents an alkyl group.

<11> In any of <2> to <10>, the pyrazine derivatives may be selected from the group consisting of 2,6-dimethylpyrazine, 2,5-dimethylpyrazine, 2,3-dimethylpyrazine, 2,3,5-trimethylpyrazine, 2,3,5,6-tetramethylpyrazine, 2-monomethylpyrazine, 2-monoethylpyrazine, 2-ethyl-6-methylpyrazine, 3-methyl-2-acetylpyrazine and 3,5-dimethyl-2-acetylpyrazine.

<12> In any of <2> to <11>, the at least one compound may be selected from the group consisting of compounds described in Table 2 below.

TABLE 2

2-ethyl-4-(2,2,3-trimethyl-3-cyclopenten-1-yl)-2-buten-1-ol
5-methyl-2-(1-methylethyl)-phenol
3,7-dimethyl-2,6-octadienal
phenylethyl salicylate
1-(5,6,7,8-tetrahydro-3,5,5,6,8,8-hexamethyl-2-naphthalenyl)-ethanone
isolongifolanone
4-(2,6,6-trimethyl-2-cyclohexen-1-yl)-3-buten-2-one (α-ionone)
4-(2,6,6-trimethyl-1-cyclohexen-1-yl)-3-buten-2-one (β-ionone)
vetiverol
7-acetyl-1,2,3,4,5,6,7,8-octahydro-1,1,6,7-tetramethyl-naphthalene
α-amylcinnamic aldehyde
α-methyl-4-(1-methylethyl)-benzenepropanal
4-methyl-3-decen-5-ol
1-(2-tert-butylcyclohexyloxy)-2-butanol <13> In any of <2> to <12>, the odor of the pyrazine derivative may be an odor generated by reaction of a skin tanning agent with skin.

<14> In <1>, at least one compound is preferably selected from the group consisting of compounds described below:
   2-ethyl-4-(2,2,3-trimethyl-3-cyclopenten-1-yl)-2-buten-1-ol
   3,7-dimethyl-2,6-octadienal
   phenylethyl salicylate
   1-(5,6,7,8-tetrahydro-3,5,5,6,8,8-hexamethyl-2-naphthalenyl)-ethanone
   Isolongifolanone
   Vetiverol
   7-acetyl-1,2,3,4,5,6,7,8-octahydro-1,1,6,7-tetramethyl-naphthalene
   α-amylcinnamic aldehyde
   α-methyl-4-(1-methylethyl)-benzenepropanal
   4-methyl-3-decen-5-ol
   2-methoxy-1-(phenylmethoxy)-4-(1-propenyl)-benzene
   α-methyl-β-(p-tert-butylphenyl)-propionaldehyde
   1(−)-menthol
   ω-6-hexadecenelactone
   2-(2-(4-methyl)-3-cyclohexen-1-yl)-propylcyclopentanone
   formaldehyde cyclododecyl ethyl acetal
   β-methyl naphthyl ketone
   cedryl acetate
   (5E)-3-methylcyclopenta-5-decen-1-one cinnamaldehyde
   4-(1-ethoxyvinyl)-3,3,5,5-tetramethylcyclohexanone
   α-hexylcinnamic aldehyde
   2-phenylpropionaldehyde
   4,7,7-trimethyl-spirobicyclo[2.2.1]heptane-2,1-cyclopentan-3-one
   cedryl methyl ether
   muscone
   2-methyl-4-(2,2,3-trimethyl-3-cyclopenten-1-yl)-2-buten-1-ol
   1-(2,6,6-trimethyl-1,3-cyclohexadien-1-yl)-2-buten-1-one
   2,4-dimethyl-3-cyclohexene-1-carboxyaldehyde
   2,4,6-trimethyl-3-cyclohexene-1-carboxyaldehyde
   3,5,6-trimethyl-3-cyclohexene-1-carboxyaldehyde
   6,10-dimethyl-3-oxa-9-undecenal
   dimethyl benzyl carbinyl acetate
   ethyl-(3aα,4α,7α,3aα)-octahydro-4,7-methano-3aH-indene-3a-carboxylate
   2-pentyl-3-methyl-2-cyclopenten-1-one
   Phenylhexanol
   6-tert-butyl-1,1-dimethylinden-4-yl methyl ketone
   cis-4-isopropylcyclohexylmethanol
   1-allyl-3-methoxy-4-hydroxybenzene
   4-tert-butyl-2,6-dimethyl-3,5-dinitroacetophenone
   1,4-dioxacycloheptadecane-5,17-dione
   hexyl salicylate
   α-methyl-3,4-methylenedioxyhydrocinnamic aldehyde <15> In <1>, at least one compound is more preferably selected from the group consisting of compounds described below:
   2-ethyl-4-(2,2,3-trimethyl-3-cyclopenten-1-yl)-2-buten-1-ol;
   3,7-dimethyl-2,6-octadienal;
   phenylethyl salicylate;
   1-(5,6,7,8-tetrahydro-3,5,5,6,8,8-hexamethyl-2-naphthalenyl)-ethanone;
   isolongifolanone;
   vetiverol;
   7-acetyl-1,2,3,4,5,6,7,8-octahydro-1,1,6,7-tetramethyl-naphthalene;
   α-amylcinnamic aldehyde;
   α-methyl-4-(1-methylethyl)-benzenepropanal;
   4-methyl-3-decen-5-ol.

EXAMPLES

The present invention will now be described more specifically by examples.

Example 1 Identification of Olfactory Receptor Responding to Pyrazine Derivative 1) Cloning of Human Olfactory Receptor Gene Human olfactory receptors were cloned based on sequence information registered in GenBank by PCR using human genomic DNA female (G1521: Promega Corporation) as a template. Each gene amplified by PCR was inserted into a pENTR vector (Invitrogen Inc.) in accordance with the manual and was recombined into the NotI and AscI site located downstream of a Flag-Rho tag sequence in a pME18S vector using the NotI and AscI site present in the pENTR vector.

2) Production of pME18S-RTP1S Vector

An RTP1S variant gene (SEQ ID NO: 3) encoding an RTP1S variant (SEQ ID NO: 4) was inserted into the EcoRI and XhoI site of a pME18S vector.

3) Production of Olfactory Receptor-Expressing Cell

HEK293 cells expressing 373 types of human olfactory receptors were produced. A reaction solution having a composition shown in Table 1 was prepared and left to stand in a clean bench for 15 min and then was dispensed in each well of a 96-well plate (Becton, Dickinson and Company). Subsequently, HEK293 cells (100 μL, $3 \times 10^5$ cells/cm$^2$) were seeded in each well and cultured in an incubator at 37° C. and 5% $CO_2$ for 24 hr.

TABLE 3

| | |
|---|---|
| OPTI-MEM (GIBCO) | 50 μL |
| Human olfactory receptor gene (incorporated in a pME18S vector having a Flag-Rho tag at the N-terminal) | 0.075 μg |
| pGL4.29 (fluc2P-CRE-hygro, Promega Corp.) | 0.03 μg |

TABLE 3-continued

| | |
|---|---|
| pGL4.75 (hRluc-CMV, Promega Corp.) | 0.03 μg |
| pME18S-RTP1S variant vector | 0.03 μg |
| Lipofectamine 2000 (Invitrogen Inc.) | 0.4 μl |

4) Luciferase Assay

An olfactory receptor expressed in HEK293 cells couples with endogenous Gαs in the cells to activate adenylate cyclase and thereby increases the amount of intracellular cAMP. In this study, the response of a pyrazine derivative was measured by luciferase reporter gene assay which monitors an increase in amount of intracellular cAMP as the luminescence value derived from a firefly luciferase gene (fluc2P-CRE-hygro). A Renilla luciferase gene was fused downstream of a CMV promoter (hRluc-CMV) and was also introduced to HEK293 cells as an internal standard to correct errors in transgenic efficiency and number of cells.

The culture medium was removed from the culture produced in the above 3), and 75 μL of a solution prepared with a CD293 medium (Invitrogen Inc.) so as to contain a pyrazine derivative (1 mM, 2,6-dimethylpyrazine) was added thereto. The cells were cultured in a $CO_2$ incubator for 2.5 hr to sufficiently express the luciferase gene in the cells. The luciferase activity was measured with a Dual-Glo™ luciferase assay system (Promega Corporation) in accordance with the operating manual of the system. The fold increases were calculated by dividing the luminescence value derived from firefly luciferase induced by stimulation with a pyrazine derivative at each concentration by the luminescence value in cells not stimulated with the pyrazine derivative and were used as an index of response strength.

5) Results

The response of each of the 373 types of the olfactory receptors to 2,6-dimethylpyrazine (1 mM) was measured, and the result showed that only olfactory receptor OR5K1 responded to 2,6-dimethylpyrazine (FIG. 1). Response of OR5K1 to 2,6-dimethylpyrazine has not been reported until now, and OR5K1 is a novel 2,6-dimethylpyrazine receptor.

Example 2 Response Characteristics of OR5K1 to Pyrazine Derivatives

Olfactory receptor OR5K1 (SEQ ID NO: 2) was expressed in HEK293 cells together with an RTP1S variant (SEQ ID NO: 4) by the same procedure as in Example 1, and the dependency of the response on the concentration (0, 3, 10, 30, 100, 300, and 1000 μM) of various pyrazine compounds was investigated. The pyrazine compounds used in this Example were pyrazine and pyrazine derivatives selected from the group consisting of 2-methylpyrazine, 2,3-dimethylpyrazine, 2,5-dimethylpyrazine, 2,3,5-trimethylpyrazine, 2,3,5,6-tetramethylpyrazine, and 2-ethylpyrazine.

The results showed that OR5K1 dose-dependently responded to the pyrazine derivatives, i.e., 2-methylpyrazine (2-MMP), 2,3-dimethylpyrazine (2,3-DMP), 2,5-dimethylpyrazine (2,5-DMP), 2,6-dimethylpyrazine (2,6-DMP), 2,3,5-trimethylpyrazine (2,3,5-TMP), 2,3,5,6-tetramethylpyrazine (2,3,5,6-TMP), and 2-ethylpyrazine (2-MEP), but did not respond to pyrazine (FIG. 2).

Example 3 Identification of Antagonist of OR5K1

Antagonistic activities of 174 test substances against olfactory receptor OR5K1 were investigated by examining response of OR5K1 to a pyrazine derivative.

2,6-Dimethylpyrazine (1 mM) and each test substance (300 μM) shown in Table 4 were added to HEK293 cells expressing olfactory receptor OR5K1 by the same procedure as in Example 2, and the response of the olfactory receptor to 2,6-dimethylpyrazine was measured to evaluate a change in response of the receptor due to addition of the test substance. Flavoring agents recognized to have cytotoxicity were re-evaluated using a mixture of 333 μM of 2,6-dimethylpyrazine and 100 μM of a test substance.

The receptor response-inhibiting rate of a test substance was calculated as follows. The receptor activity (X-Y) by stimulation with 2,6-dimethylpyrazine alone was determined by subtracting the luminescence value (Y) in cells to which the receptor was introduced but were not stimulated with 2,6-dimethylpyrazine from the luminescence value (X) derived from firefly luciferase induced by stimulation with 2,6-dimethylpyrazine alone. Similarly, the receptor activity (Z-Y) in the presence of a test substance was determined by subtracting the luminescence value (Y) in cells not stimulated with 2,6-dimethylpyrazine from the luminescence value (Z) stimulated with a mixture of 2,6-dimethylpyrazine and the test substance. The reduction rate of the receptor activity (Z-Y) in the presence of a test substance to the receptor activity (X-Y) by stimulation with 2,6-dimethylpyrazine alone was calculated by the following computation expression:

Inhibition rate (%)={1−(Z−Y)/(X−Y)}×100, to determine the receptor response-inhibiting rate of the test substance. In the measurement, multiple independent experiments were performed in duplicate, and the average of each experiment was used.

As shown in Table 4, the results showed that 56 test substances had antagonistic activity on the response of OR5K1 to 2,6-dimethylpyrazine.

TABLE 4

| Inhibition rate: 75% or more (exceptionally-strong antagonist) | Inhibition rate: 50% or more (strong antagonist) | Inhibition rate: 40% or more (weak antagonist) |
|---|---|---|
| 2-ethyl-4-(2,2,3-trimethyl-3-cyclopenten-1-yl)-2-buten-1-ol (bacdanol) | 2-methoxy-1-(phenylmethoxy)-4-(1-propenyl)-benzene (benzyl isoeugenol) | cyclopentadecanolide (pentalide) |
| 5-methyl-2-(1-methylethyl)-phenol (thymol) | α-methyl-β-(p-tert-butylphenyl)-propionaldehyde (lilial) | 1-(2,6,6-trimethyl-1,3-cyclohexadien-1-yl)-2-buten-1-one(damascenone) |
| 3,7-dimethyl-2,6-octadienal (citral) | l(−)-menthol | 2,4-dimethyl-3-cyclohexene-1-carboxyaldehyde (triplal) |
| phenylethyl salicylate | ω-6-hexadecenelactone (ambrettolide) | isocyclocitral |
| 1-(5,6,7,8-tetrahydro-3,5,5,6,8,8-hexamethyl-2-naphthalenyl)-ethanone (Tonalid (registered trademark), tentarome) | 2-(2-(4-methyl)-3-cyclohexen-1-yl)-propylcyclopentanone (nectaryl) | 6,10-dimethyl-3-oxa-9-undecenal (citronellyl oxyacetaldehyde) |
| | cyclododecyl ethyl acetal (Boisambrene Forte (registered trademark)) | dimethyl benzyl carbinyl acetate |
| | 1-(2,3,4,7,8,8a-hexahydro-3,6,8,8-tetramethyl-1H-3a,7-methanoazulen-5-yl)-ethanone (acetyl cedrene) | ethyl-(3aα,4α,7α,3aα)-octahydro-4,7-methano-3aH-indene-3a-carboxylate (Fruitate (registered trademark)) |
| Isolongifolanone | | |
| 4-(2,6,6-trimethyl-2-cyclohexen-1-yl)-3-buten-2-one (α-ionone) | β-methyl naphthyl ketone | 2-pentyl-3-methyl-2-cyclopenten-1-one (dihydrojasmon) |
| 4-(2,6,6-trimethyl-1-cyclohexen-1-yl)-3-buten-2-one (β-ionone) | cedryl acetate (5E)-3-methylcyclopenta-5-decen-1-one (δ-muscenone) | |
| vetiverol | cinnamaldehyde | phenylhexanol 1-(5,5-dimethyl- |

TABLE 4-continued

| Inhibition rate: 75% or more (exceptionally-strong antagonist) | Inhibition rate: 50% or more (strong antagonist) | Inhibition rate: 40% or more (weak antagonist) |
|---|---|---|
| 7-acetyl-1,2,3,4,5,6,7,8-octahydro-1,1,6,7-tetramethyl-naphthalene (Iso E Super) α-amylcinnamic aldehyde α-methyl-4-(1-methylethyl)-benzenepropanal (cyclamen aldehyde) 4-methyl-3-decen-5-ol (undecavertol) 1-(2-tert-butylcyclohexyloxy)-2-butanol (Amber Core (registered trademark)) | 4-(1-ethoxyvinyl)-3,3,5,5-tetramethyl-cyclohexanone (kephalis) α-hexylcinnamic aldehyde 2-phenylpropional-dehyde (hydratropic aldehyde) 3,7-dimethyl-6-octenal (citronellal) dodecahydro-3a,6,6,9a-tetramethyl-naphtho[2,1-b]furan (Ambrotech (registered trademark)) 4,7,7-trimethyl-spirobicyclo[2.2.1]heptane-2,1-cyclopentan-3-one (Sagetone (registered trademark) V) α-isomethyl ionone (γ-methyl ionone) 3,7-dimethyl-1-octanol (tetrahydrogeraniol) cedryl methyl ether muscone 2-methyl-4-(2,2,3-trimethyl-3-cyclopenten-1-yl)-2-buten-1-ol (Sandalmysore Core (registered trademark)) 2-cyclohexylpropanal (Pollenal (registered trademark) II) γ-undecalactone | 1-cyclohexen-1-yl)-4-penten-1-one (Dynascone (registered trademark)) 6-tert-butyl-1,1-dimethylinden-4-yl methyl ketone (celestolide) cis-4-isopropyl-cyclohexyl-methanol (mayol) 1-allyl-3-methoxy-4-hydroxybenzene (eugenol) (E)-3,7-dimethyl-2,6-octadien-1-ol (geraniol) 4-tert-butyl-2,6-dimethyl-3,5-dinitro-acetophenone (musk ketone) 1,4-dioxacyclo-heptadecane-5,17-dione (ethylene brassylate) hexyl salicylate α-methyl-3,4-methylenedioxy-hydrocinnamic aldehyde (helional) |

Example 4 Evaluation of Ability of Antagonist of OR5K1 for Reducing Odors of Pyrazine Derivatives The abilities to reduce an odor of a pyrazine derivative by the antagonist substances identified in Example 3 were confirmed by a sensory test.

A flavoring agent (0.5 μL) was added to cloth (0.5 g) containing 2,6-dimethylpyrazine (1%), and the odor thereof was evaluated by comparing the strength of odor of 2,6-dimethylpyrazine of the cloth not applied with flavor by the flavoring agent. The sensory evaluation test was performed by four panelists. In the evaluation, a case where a strong odor of 2,6-dimethylpyrazine was smelled was rated as 1, and a case where the odor of 2,6-dimethylpyrazine was not smelled at all was rated as 5.

Figure 3:
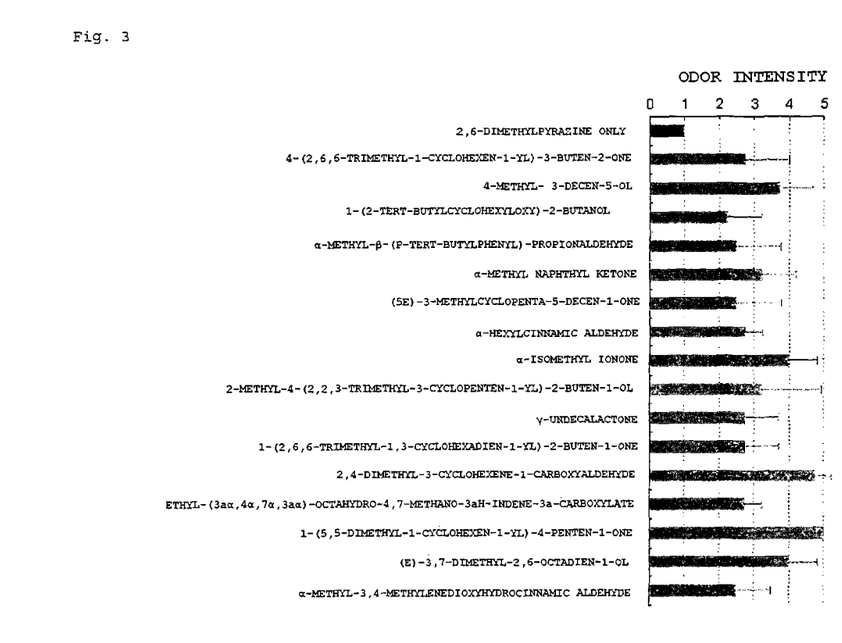
FIG. 3 shows effects of various compounds for reducing an odor of 2,6-dimethylpyrazine, wherein error bar=±SE.

As a result, the odor of 2,6-dimethylpyrazine was inhibited by the antagonists which were revealed in Example 3 to inhibit the response of OR5K1 to 2,6-dimethylpyrazine, that is, the odor of 2,6-dimethylpyrazine was inhibited by 4-(2,6,6-trimethyl-1-cyclohexen-1-yl)-3-buten-2-one ((β-ion-one), 4-methyl-3-decen-5-ol (undecavertol), 1-(2-tert-butyl-cyclohexyloxy)-2-butanol (Amber Core (registered trademark)), α-methyl-β-(p-tert-butylphenyl)-propionaldehyde (lilial), β-methyl naphthyl ketone, (5E)-3-methylcy-clopenta-5-decen-1-one (δ-muscenone), α-hexylcinnamic aldehyde, α-isomethyl ionone (γ-methyl ionone), 2-methyl-4-(2,2,3-trimethyl-3-cyclopenten-1-yl)-2-buten-1-ol (Sandalmysore Core (registered trademark)), γ-undecalactone, 1-(2,6,6-trimethyl-1,3-cyclohexadien-1-yl)-2-buten-1-one (damascenone), 2,4-dimethyl-3-cyclohexene-1-carboxyaldehyde (triplal), ethyl-(3aα,4α,7α,3aα)-octahydro-4,7-methano-3aH-indene-3a-carboxylate (Fruitate (registered trademark)), 1-(5,5-dimethyl-1-cyclohexen-1-yl)-4-penten-1-one (Dynascone (registered trademark)), (E)-3,7-dimethyl-2,6-octadien-1-ol (geraniol), and α-methyl-3,4-methylenedioxyhydrocinnamic aldehyde (helional) (FIG. 3).

The embodiments of the present invention have been described above, but it should be understood that the specific embodiments described above are not intended to limit the present invention. Various other changes and modifications within the scope of the present invention are obvious to those skilled in the art.

The documents and patent applications cited in this specification are incorporated by reference herein in their entirety.

What is claimed is:

1. A method of reducing an odor of a pyrazine derivative having the formula (I), wherein $R_1$ represents methyl, ethyl, or acetyl; and $R_2$, $R_3$, and $R_4$ each independently represent hydrogen or methyl,
wherein the method comprises providing the pyrazine derivative and providing at least one compound selected from the group consisting of the following compounds:
2-ethyl-4-(2,2,3-trimethyl-3-cyclopenten-1-yl)-2-buten-1-ol
and 4-methyl-3-decen-5-ol;
wherein said compound antagonizes the response of olfactory receptor OR5K1 to the pyrazine derivative.

2. The method according to claim 1, which comprises applying at least one compound to an individual in need of reduction of the odor of the pyrazine derivative, in the presence of the odor of the pyrazine derivative.

3. The method according to claim 2, wherein the at least one compound inhibits responses of an olfactory receptor OR5K1.

4. The method according to claim 1, wherein at least one of $R_1$, $R_2$, $R_3$ and $R_4$ is as follows: $R_1$ is methyl or ethyl; $R_2$, $R_3$ and $R_4$ each independently represent methyl.

5. The method according to claim 1, wherein the pyrazine derivative is selected from the group consisting of 2,6-dimethylpyrazine, 2,5-dimethylpyrazine, 2,3-dimethylpyrazine, 2,3,5-trimethylpyrazine, 2,3,5,6-tetramethylpyrazine, 2-monomethylpyrazine, 2-monoethylpyrazine, 2-ethyl-6-methylpyrazine, 3-methyl-2-acetylpyrazine, and 3,5-dimethyl-2-acetylpyrazine.

6. A method of antagonizing responses of an olfactory receptor OR5K1, wherein the method includes applying, to an olfactory receptor OR5K1, at least one compound selected from the group consisting of the following compounds:
2-ethyl-4-(2,2,3-trimethyl-3-cyclopenten-1-yl)-2-buten-1-ol;
and
4-methyl-3-decen-5-ol.

7. The method according to claim 1, wherein the pyrazine derivative is 2,6-dimethylpyrazine.

* * * * *

SEQUENCE LISTING

```
<160> NUMBER OF SEQ ID NOS: 4

<210> SEQ ID NO 1
<211> LENGTH: 927
<212> TYPE: DNA
<213> ORGANISM: Homo sapiens

<400> SEQUENCE: 1
atggctgaag aaaatcatac catgaaaaat gagtttatcc tcacaggatt tacagatcac      60
cctgagctga agactctgct gtttgtggtg ttctttgcca tctatctgat caccgtggtg     120
gggaatatta gtttggtggc actgatattt acacaccgtc ggcttcacac accaatgtac     180
atctttctgg gaaatctggc tcttgtggat tcttgctgtg cctgtgctat tacccccaaa     240
```

```
atgttagaga acttctttc tgagaacaaa aggatttccc tctatgaatg tgcagtacag    300 tttattttc tttgcactgt ggaaactgca gactgctttc ttctggcagc aatggcctat    360
gaccgctatg tggccatatg caacccactg cagtaccaca tcatgatgtc caagaaactc    420
tgcattcaga tgaccacagg ggccttcata gctggaaacc tgcattccat gattcatgta    480
gggcttgtat ttaggttagt tttctgtgga tcgaatcaca tcaaccactt ttactgtgat    540
attcttccct tgtatagact ctcttgtgtt gatccttata tcaatgaact ggttctattc    600
atcttctcag gttcagttca agtctttacc ataggtagtg tcttaatatc ttatctctat    660
attcttctta ctattttcaa aatgaaatcc aaagagggaa gggccaaagc ttttttctacc    720 tgtgcatccc actttttgtc agtttcatta ttctatggat ctcttttctt catgtacgtt    780
agaccaaatt tgcttgaaga aggggataaa gatataccag ctgcaatttt atttacaata    840
gtagttccct tactaaatcc tttcatttat agcctgagaa atagggaagt aataagtgtc    900
ttaagaaaaa ttctgatgaa gaaataa                                       927
```

<210> SEQ ID NO 2  
<211> LENGTH: 288  
<212> TYPE: PRT  
<213> ORGANISM: Homo sapiens

<400> SEQUENCE: 2

```
Met Ala Glu Glu Asn His Thr Met Lys Asn Glu Phe Ile Leu Thr Gly
1               5                   10                  15

Phe Thr Asp His Pro Glu Leu Lys Thr Leu Leu Phe Val Val Phe Phe
            20                  25                  30

Ala Ile Tyr Leu Ile Thr Val Val Gly Asn Ile Ser Leu Val Ala Leu
        35                  40                  45

Ile Phe Thr His Arg Arg Leu His Thr Pro Met Tyr Ile Phe Leu Gly
    50                  55                  60

Asn Leu Ala Leu Val Asp Ser Cys Cys Ala Cys Ala Ile Thr Pro Lys
65                  70                  75                  80

Met Leu Glu Asn Phe Phe Ser Glu Asn Lys Arg Ile Ser Leu Tyr Glu
                85                  90                  95

Cys Ala Val Gln Phe Tyr Phe Leu Cys Thr Val Glu Thr Ala Asp Cys
            100                 105                 110

Phe Leu Leu Ala Ala Met Ala Tyr Asp Arg Tyr Val Ala Ile Cys Asn
        115                 120                 125

Pro Leu Gln Tyr His Ile Met Met Ser Lys Lys Leu Cys Ile Gln Met
    130                 135                 140

Thr Thr Gly Ala Phe Ile Ala Gly Asn Leu His Ser Met Ile His Val
145                 150                 155                 160

Gly Leu Val Phe Arg Leu Val Phe Cys Gly Ser Asn His Ile Asn His
                165                 170                 175

Phe Tyr Cys Asp Ile Leu Pro Leu Tyr Arg Leu Ser Cys Val Asp Pro
            180                 185                 190

Tyr Ile Asn Glu Leu Val Leu Phe Ile Phe Ser Gly Ser Val Gln Val
        195                 200                 205

Phe Thr Ile Gly Ser Val Leu Ile Ser Tyr Leu Tyr Ile Leu Leu Thr
    210                 215                 220

Cys Ala Ser His Phe Leu Ser Val Ser Leu Phe Tyr Gly Ser Leu Phe
225                 230                 235                 240

Phe Met Tyr Val Arg Pro Asn Leu Leu Glu Glu Gly Asp Lys Asp Ile
                245                 250                 255
```

```
Pro Ala Ala Ile Leu Phe Thr Ile Val Val Pro Leu Leu Asn Pro Phe
            260                 265                 270

Ile Tyr Ser Leu Arg Asn Arg Glu Val Ile Ser Val Leu Arg Lys Ile
        275                 280                 285
```

<210> SEQ ID NO 3
<211> LENGTH: 681
<212> TYPE: DNA
<213> ORGANISM: Homo sapiens

<400> SEQUENCE: 3

```
atgtgcaagt ccctgacaac gggagagtgg aagaagatct tctacgagaa aatggaggag    60
gtgaaacccg cagactcctg ggacctgatc atggatccca acctccagca taacgtattg   120
gcccccggat ggaagcagta cctggagcag cacgcctctg ccgcttcca ctgctcctgg    180
tgctggcata gctggcagtc ctcccaactg gtgatcctct ccacatgta cctggataag    240
acccagcgga cgggctgcgt gcgcatgaga gtcttcaagc agctctgcta cgagtgtggc   300
tcctcccggc tggacgagtc gtccatgctg aggagaaca tagagggct ggtggacaac     360
ctcgtctgca gcctccggga gcagtgctac ggggagaatg ggggacagta ccgcatccac   420
gtggcctccc gccaagacca ccagcgccac cggggagagt tctgcgaggc ctgccgcctg   480
ggcatcaccc actggaagcc cacggagaag atgctagagg aggaggcctc cacctacacc   540
ttctcccggc tgcgaatcc ttccaagaca gccgactcgg gtttcagctg tgacttctgc    600
tccctccctt ggtgtatgtt ctgggccacg gtgctcttgc tcatcatata cctgcagatc   660
tccttcggca accctgtcta a                                              681
```

<210> SEQ ID NO 4
<211> LENGTH: 226
<212> TYPE: PRT
<213> ORGANISM: Homo sapiens

<400> SEQUENCE: 4

```
Met Cys Lys Ser Leu Thr Thr Gly Glu Trp Lys Lys Ile Phe Tyr Glu
1               5                   10                  15

Lys Met Glu Glu Val Lys Pro Ala Asp Ser Trp Asp Leu Ile Met Asp
            20                  25                  30

Pro Asn Leu Gln His Asn Val Leu Ala Pro Gly Trp Lys Gln Tyr Leu
        35                  40                  45

Glu Gln His Ala Ser Gly Arg Phe His Cys Ser Trp Cys Trp His Ser
    50                  55                  60

Trp Gln Ser Ser Gln Leu Val Ile Leu Phe His Met Tyr Leu Asp Lys
65                  70                  75                  80

Thr Gln Arg Thr Gly Cys Val Arg Met Arg Val Phe Lys Gln Leu Cys
                85                  90                  95

Tyr Glu Cys Gly Ser Ser Arg Leu Asp Glu Ser Ser Met Leu Glu Glu
            100                 105                 110

Asn Ile Glu Gly Leu Val Asp Asn Leu Val Cys Ser Leu Arg Glu Gln
        115                 120                 125

Cys Tyr Gly Glu Asn Gly Gly Gln Tyr Arg Ile His Val Ala Ser Arg
    130                 135                 140

Gln Asp His Gln Arg His Arg Gly Glu Phe Cys Glu Ala Cys Arg Leu
145                 150                 155                 160

Gly Ile Thr His Trp Lys Pro Thr Glu Lys Met Leu Glu Glu Glu Ala
                165                 170                 175
```

```
Ser Thr Tyr Thr Phe Ser Arg Pro Ala Asn Pro Ser Lys Thr Ala Asp
            180                 185                 190

Ser Gly Phe Ser Cys Asp Phe Cys Ser Leu Pro Trp Cys Met Phe Trp
        195             200                 205

Ala Thr Val Leu Leu Leu Ile Ile Tyr Leu Gln Ile Ser Phe Gly Asn
    210             215                 220

Pro Val
225
```